United States Patent [19]

Okada et al.

[11] Patent Number: 4,824,373
[45] Date of Patent: Apr. 25, 1989

[54] SWAGED METAL DENTURE BASE

[75] Inventors: Minoru Okada; Yoshiaki Shida; Tomio Nishikawa, all of Amagasaki; Isamu Kato, Kawanishi; Kazuyuki Nakano, Kawanishi; Ryozo Isomura, Kawanishi, all of Japan

[73] Assignees: Sankin Industry Co.; Sumitomo Metal Industries, Ltd., both of Japan

[21] Appl. No.: 103,648

[22] Filed: Oct. 2, 1987

[30] Foreign Application Priority Data

Oct. 8, 1986 [JP] Japan .................................. 61-240024

[51] Int. Cl.⁴ .............................................. A61C 13/00
[52] U.S. Cl. .................................. 433/200.1; 433/171; 164/DIG. 4
[58] Field of Search ...................... 433/167, 171, 199.1, 433/200.1, 34; 164/DIG. 4; 249/54

[56] References Cited

U.S. PATENT DOCUMENTS 3,600,752  8/1971  Kopp ...................................... 433/34

FOREIGN PATENT DOCUMENTS 3610349  10/1987  Fed. Rep. of Germany ........ 433/34
57-02828   9/1982  Japan ................................ 433/199.1
1199244  12/1985  U.S.S.R. ............................. 433/213

Primary Examiner—John J. Wilson
Assistant Examiner—Adriene J. Lepiane
Attorney, Agent, or Firm—Lorusso & Loud

[57] ABSTRACT

A denture base of pressure-formed, superplastic alloy plate, and a method of making a metal denture base, includes providing a superplastic alloy plate and a female die having a finishing surface, and pressure-forming the alloy plate on the finishing surface of the female die at a temperature where the alloy exhibits superplasticity.

13 Claims, 1 Drawing Sheet

SWAGED METAL DENTURE BASE

BACKGROUND OF THE INVENTION

This invention relates to a swaged metal denture base and a method for making the same.

Typical conventional metal denture bases are made of a Co—Cr alloy or a Ni—Cr alloy which alloys can be easily shaped with precision. The manufacture of such cast denture bases has the following disadvantages:

(a) It is difficult to produce a thin denture base;
(b) the incidence of defective products is bad; and
(c) a long fettling time is required because the surfaces of a cast product are not smooth.

In order to eliminate such disadvantages in the manufacture of the cast denture base, it has been recently proposed that a swaged metal denture base be made by cold-forming a stainless steel plate or a pure titanium plate. However, an expensive press machine is required for the manufacture of such a swaged denture base. In addition, the method of manufacture includes plural complicated steps. For example, there must be a rubber press step, a metal press step and a fitting press step. An annealing step is also necessary in order to eliminate work-hardening problems. A pair of male and female precision dies must be provided for each pressing step.

Nevertheless, the cold-forming (press-forming) of a denture base as described above provides less precision as compared with a cast denture base. It is difficult to obtain a swaged denture base which can be precisely fitted to an individual's oral cavity, mainly because the metal plate has spring back characteristics.

SUMMARY OF THE INVENTION

Accordingly, it is an object of the present invention to provide a precision fit denture base and an efficient method of cold-forming same with a high degree of accuracy.

According to this invention, a denture base is made by pressure-forming a plate of an alloy having superplasticity. The definition of "superplasticity," as used herein is that found in the *McGraw-Hill Encyclopedia of Science and Technology* (5th Ed.) which reads:

"The unusual ability of some metals and alloys to elongate uniformly thousands of percent at elevated temperatures, much like hot polymers or glasses."

As further explained in that treatise:

"Under normal creep conditions, conventional alloys do not stretch uniformly, but form a necked-down region and then fracture after elongations of only 100% or less."

It is preferably that the alloy plate is an alpha + beta type titanium alloy such as a Ti-6Al-4V alloy, or two-phase stainless steel such as a delta + gamma two-phase stainless steel disclosed in the magazine "Iron and Steel" (1984), No. 15, pages 378 to 385, because such alloys are nontoxic and have good corrosion resistance and high strength.

The method of making such a metal denture base, includes placing an alloy plate having a superplasticity facing a female die having a finishing surface, and pressure-forming the alloy plate on the finishing surface of the female die at a temperature where the alloy plate exhibits a superplasticity. For example, after a first side of the alloy plate is set facing the finishing surface of the female die, the opposite side of the alloy plate receives a pressure that is higher than the pressure received at the first side whereby the alloy plate is subjected to superplastic deformation on the finishing surface of the female die.

The alloy plate is preferably pressure-formed, using, as a pressure source, an inert gas, nitrogen gas, molten salt or a molten slag which does not react with the alloy plate. During pressure-forming the space between the alloy plate and the die can be evacuated.

The female die is preferably made of a refractory material such as zirconia, alumina, silica or a combination thereof because superplasticity temperatures are relatively high and dies are relatively easily fabricated from such ceramics. The female die preferably has substantially the same coefficient of thermal expansion as the alloy plate.

The present invention offers many advantages. For example, because the alloy plate has superplasticity, it can be efficiently and precisely fitted to an individual oral cavity without use of any male die even if the finishing surface of the female die has an intricate shape. As the superplasticity temperature is relatively high in case of an alpha + beta type titanium alloy or a two-phase stainless steel, only a small strain energy remains so that no stress relief annealing step is necessary after formation.

Any die conventionally used to form a cast denture base can be used as the female die in the present invention. Thus, it is very easy to make a female die for a precise fit of the plate into an oral cavity.

As the alloy plate is pressure-formed, poor run in casting, shrinkage voids and like problems associated with casting techniques can be avoided. Surface smoothness of the product is also better. A thin base can be easily obtained.

The swaged metal denture base according to this invention can be produced at a low cost using a small number of manufacturing steps.

DESCRIPTION OF EMBODIMENTS

Figure 1:
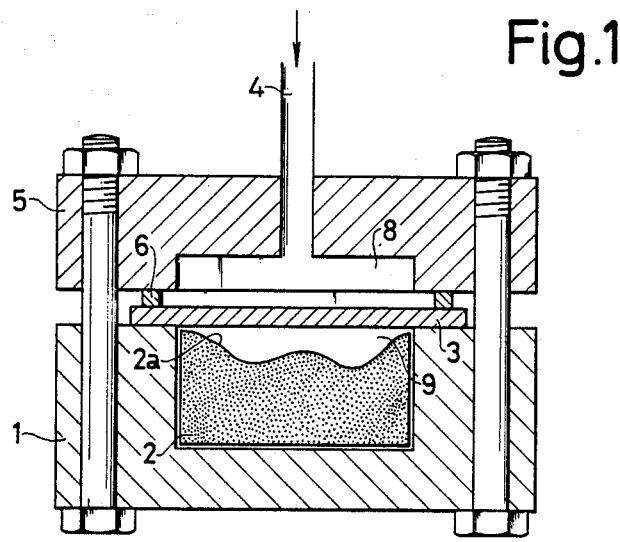
FIG. 1 is an elevational view in cross-section of an apparatus for making a swaged metal denture base according to this invention.
Figure 3:
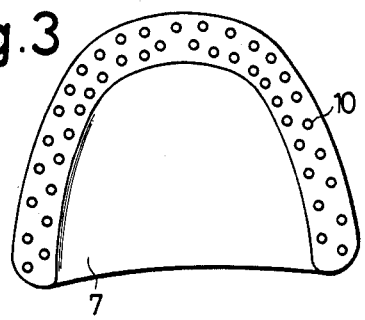
FIG. 3 is a plan view of the swaged metal denture base of the present invention.

FIG. 1 illustrates the pressure-forming of a superplastic alloy plate in the manufacture of a swaged metal denture base according to the present invention.

A hermetically sealed mold 1 is provided with a female die 2 made of a refractory material as described above so as to provide a precise fit for an oral cavity. An alloy plate 3 having superplasticity is set facing the female die 2. The alloy plate 3 is preferably a Ti-6Al-4V alloy. A conduit 4 provides fluid communication through mold closure 5. A gasket 6 is disposed between the closure 5 and the alloy 3 to provide a hermetic seal.

In order to avoid oxidation of the alloy plate 3, the spaces 8, 9 in the mold are evacuated or filled with an inert gas and then heated to the superplasticity temperature of the Ti-6Al-4V alloy. When the alloy plate 3 is heated to a temperature where it exhibits superplasticity, the inert gas or molten-salt liquid flows into the space 8 so as to press the alloy plate 3 onto the finishing surface 2a of the female die 2. The alloy plate 3 is superplasticly pressure-formed on the finishing surface 2a of the female die 2. The shaped alloy plate 3 has a smooth surface which can be easily polished. No stress relief annealing step is necessary.

EXAMPLE

Three plates as described in Table 1 were prepared. A female die made of a refractory material was prepared so as to correspond in shape to an oral cavity. The composition of each material is shown in Table 1.

Each plate and each female die were set in a mold 1 as shown in FIG. 1. Under the condition given in Table 2, the plates were shaped into swaged metal denture bases. Test results for the denture bases are shown in Table 2 and compared with test results for two conventional denture bases.

The shaped denture base 7 has a flange portion in which plural through-holes 10 are formed.

Figure 2:
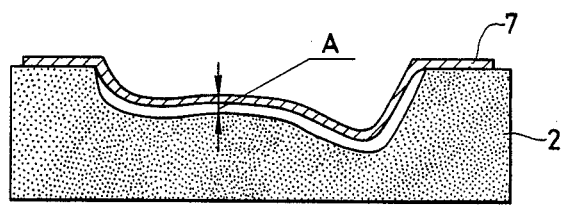
FIG. 2 is an elevational view in cross-section showing the relationship between a swaged metal denture base and a female die during forming in accordance with the present invention.

The product accuracy was determined by measuring clearance A between the shaped denture base 7 and the female die 2 as shown in FIG. 2. Such a clearance A occurs due to the spring back of the plate. In the case of a conventional cold-pressing method, the clearance A is 50–500 microns. In the present invention, the clearance A has been found to be only 5 to 100 microns.

As can be seen from Table 2, a denture base according to this invention is accurate in shape and provides an excellent fit with a given oral cavity. As only a short polishing time and no stress relief annealing are required, the production cost is very low.

TABLE 1

Composition of the Material (wt. %)

| Type | Al | V | Sn | Fe | Cu | O | H | N | C |
|---|---|---|---|---|---|---|---|---|---|
| A | 6.1 | 4.0 | — | 0.13 | — | 0.12 | 0.005 | 0.01 | 0.01 |

| Ti + other impurities | thickness (mm) | compositions of plate |
|---|---|---|
| balance | 0.4 | Ti—6Al—4V |

| Type | Al | V | Sn | Fe | Cu | O | H | N | C |
|---|---|---|---|---|---|---|---|---|---|
| B | 5.7 | 5.6 | 2.1 | 0.52 | 0.55 | 0.13 | 0.005 | 0.01 | 0.01 |

| Ti + other impurities | thickness (mm) | compositions of plate |
|---|---|---|
| balance | 0.3 | Ti—6Al—6V—2Sn |

| Type | C | Si | Mn | P | S | Ni | Cr | Mo | Cu | W | N |
|---|---|---|---|---|---|---|---|---|---|---|---|
| C | 0.02 | 0.45 | 0.80 | 0.02 | 0.001 | 6.8 | 24.5 | 2.8 | 0.4 | 0.3 | 0.15 |

| Fe + other impurities | thickness (mm) | compositions of plate |
|---|---|---|
| balance | 0.4 | two-phase stainless steel |

TABLE 2

| | | | Shaping Parameters | | | |
|---|---|---|---|---|---|---|
| Items | | Plate | Pressurized fluid | Shaping temperature (°C.) | Shaping pressure | Atmosphere |
| Examples of this invention | 1 | A | Argon gas | 850 | 6 kgf/cm$^2$ | Vacuum |
| | 2 | B | Nitrogen gas | 800 | 8 kgf/cm$^2$ | Argon |
| | 3 | C | Molten slag SiO$_2$: 34% CaO: 29% F: 17% others | 950 | 9 kgf/cm$^2$ | Air |
| Prior art | 4 | Co—Cr alloy | Casting an ingot | | | |
| | 5 | Pure Ti | Cold-pressing a plate of 0.4 mm thickness | | | |

| | | | Shaping Parameters | | |
|---|---|---|---|---|---|
| Items | | Plate | Shaping time | Material of die | Mold |
| Examples of this invention | 1 | A | 0.5 hr. | Matrix Material: Zirconium Oxide + Alumina Binder: Magnesium Oxide + primary ammonium phosphate | only female die |
| | 2 | B | 2 hr. | | |
| | 3 | C | 3 hr. | Matrix Material: Silica + Cristobalite Binder: Magnexium Oxide + primary ammonium phosphate | |
| Prior art | 4 | Co—Cr alloy | | Same as Example 3 | femele die + sunk material |
| | 5 | Pure Ti | | Rubber and die steel (various dies are used) | many male and female dies |

| | | | Test results | | | | |
|---|---|---|---|---|---|---|---|
| Items | | Plate | Accuracy | Fitness | Smoothness | Polishing time | Stress relief annealing |
| Examples of this invention | 1 | A | 0 | 0 | 0 | 0.1–1 hr. | not necessary |
| | 2 | B | | | | | |
| | 3 | C | | | | | |
| Prior art | 4 | Co—Cr alloy | 0 | 0 | X | 2–4 hr. | not necessary |
| | 5 | Pure Ti | X | X | 0 | 0.5–1 hr. | necessary |

We claim:

1. A denture base having a flange portion in which plural openings are formed, the denture base being a pressure-formed, superplastic alloy plate and having a polished, smooth surface, the alloy plate being pressure-formed at a temperature where the alloy exhibits superplasticity.

2. The denture base of claim 1, wherein the alloy is an alpha + beta type titanium alloy.

3. The denture base of claim 1, wherein the alloy is a two-phase stainless steel.

4. A method of making a metal denture base, comprising the steps of: providing a superplastic alloy plate and a female die having a finishing surface; and pressure-forming the alloy plate on the finishing surface of the female die at a temperature where the alloy exhibits superplasticity.

5. The method of claim 4, wherein the pressure imposed on the side of the alloy plate facing the female die is less than that imposed on the opposite side of the plate whereby the alloy plate is subjected to superplastic pressure-forming on the finishing surface of the female die.

6. The method of claim 5, wherein fluid pressure is imposed on said plate to form same, wherein said fluid is selected from the group consisting of inert gas, nitrogen gas, a molten-salt liquid or a molten-slag liquid.

7. The method of claim 4, wherein the alloy is an alpha + beta type titanium alloy.

8. The method of claim 7, wherein the female die is made of a refractory material, wherein said refractory material is selected from the group consisting of zirconia, alumina, silica or a combination thereof.

9. The method of claim 4, wherein the alloy is a two-phase stainless steel.

10. The method of claim 9, wherein the female die is made of a refractory material, wherein said refractory material is selected from the group consisting of zirconia, alumina, silica or a combination thereof.

11. The method of claim 4, wherein fluid pressure is imposed on said plate to form same, wherein said fluid is selected from the group consisting of inert gas, nitrogen gas, a molten-salt liquid or a molten-slag liquid.

12. The method of claim 11, wherein the female die is made of a refractory material, wherein said refractory material is selected from the group consisting of zirconia, alumina, silica or a combination thereof.

13. The method of claim 4, wherein the female die is made of a refractory material, wherein said refractory material is selected from the group consisting of zirconia, alumina, silica or a combination thereof.

* * * * *